United States Patent
Dinkel et al.

(10) Patent No.: US 9,568,393 B2
(45) Date of Patent: Feb. 14, 2017

(54) METHOD AND DEVICE FOR THE EARLY DETECTION OF CRACK FORMATIONS IN MEDIA-CARRYING WORKPIECES

(71) Applicant: WERKZEUGBAU SIEGFRIED HOFMANN GMBH, Lichtenfels/Ofr. (DE)

(72) Inventors: Michael Dinkel, Bad Staffelstein-Uetzing (DE); Stefan Hofmann, Lichtenfels (DE)

(73) Assignee: Werkzeugbau Siegfried Hofmann GmbH, Lichtenfels/Oberfranken (DE)

( * ) Notice: Subject to any disclaimer, the term of this patent is extended or adjusted under 35 U.S.C. 154(b) by 0 days.

(21) Appl. No.: 14/497,583

(22) Filed: Sep. 26, 2014

(65) Prior Publication Data
US 2015/0090045 A1  Apr. 2, 2015

(30) Foreign Application Priority Data
Sep. 30, 2013  (DE) .................. 10 2013 016 166

(51) Int. Cl.
*G01N 3/00* (2006.01)
*G01M 3/32* (2006.01)
(Continued)

(52) U.S. Cl.
CPC ......... *G01M 3/3272* (2013.01); *G01M 5/0033* (2013.01); *G01M 5/0075* (2013.01);
(Continued)

(58) Field of Classification Search
CPC  G01M 3/3272; G01M 5/0033; G01M 5/0075; G01N 19/08
(Continued)

(56) References Cited

U.S. PATENT DOCUMENTS

| 1,052,392 A | 2/1913 | Van Dyken |
| 2,185,315 A | 1/1940 | Rogatchoff |
| (Continued) | | |

FOREIGN PATENT DOCUMENTS

| DE | 3228548 A1 | 6/1983 |
| DE | 19740502 A1 | 3/1999 |
| (Continued) | | |

OTHER PUBLICATIONS

Mai G., "Weg vom Kühlkanal", Formenbau, Plastverarbeiter, Huetig GmbH, Heidelberg, DE, (Feb. 1, 2006), ISSN 0032-1338, pp. 72-73—Statement of Relevance.

*Primary Examiner* — Max Noori
(74) *Attorney, Agent, or Firm* — Laurence A. Greenberg; Werner H. Stemer; Ralph E. Locher

(57) ABSTRACT

A device is provided for the early detection of crack formations in work pieces or in components that are subjected to mechanical loading. Wherein in the region of at least one surface at risk of cracking there is arranged at least one testing chamber that is formed by a generative process of manufacturing the work piece or a portion of a work piece and to which a testing medium under pressure is admitted. Either a pressure sensor for determining a drop in pressure resulting from a crack formation of the work piece is connected to the testing chamber or a gas sensor that can also react to a testing medium escaping from the testing chamber in the event of crack formation is arranged in the vicinity of the testing chamber.

16 Claims, 3 Drawing Sheets

(51) Int. Cl.
  *G01M 5/00* (2006.01)
  *G01N 19/08* (2006.01)
(52) U.S. Cl.
  CPC ..... *G01N 19/08* (2013.01); *G01N 2203/0062* (2013.01); *Y10T 29/49993* (2015.01)
(58) Field of Classification Search
  USPC .................................................. 73/799, 808
  See application file for complete search history.

(56) References Cited

U.S. PATENT DOCUMENTS

| | | | |
|---|---|---|---|
| 4,031,751 A * | 6/1977 | Haddad | E21B 47/10 73/152.23 |
| 4,447,388 A | 5/1984 | Sutton, Jr. | |
| 4,448,080 A | 5/1984 | Dressel et al. | |
| 6,196,056 B1 * | 3/2001 | Ewing | G01M 3/226 73/40.7 |
| 6,729,797 B2 | 5/2004 | Manger et al. | |
| 7,186,331 B2 * | 3/2007 | Maartens | B01D 65/102 210/137 |
| 2005/0257833 A1 | 11/2005 | Folkers | |
| 2008/0081000 A1 * | 4/2008 | MacLeod | G01M 3/329 422/68.1 |
| 2009/0084188 A1 | 4/2009 | Seitza et al. | |
| 2011/0071770 A1 * | 3/2011 | Telgkamp | G01M 5/0033 702/35 |
| 2013/0081449 A1 * | 4/2013 | Li | G01M 3/2815 73/40.5 R |

FOREIGN PATENT DOCUMENTS

| | | |
|---|---|---|
| DE | 102009027807 A1 | 3/2011 |
| EP | 1547749 A1 | 6/2005 |
| EP | 1777479 A2 | 4/2007 |
| EP | 2045065 A2 | 4/2009 |
| JP | H09254188 A | 9/1997 |
| JP | 2005300498 A | 10/2005 |
| JP | 2013035204 A | 2/2013 |
| WO | 2007144458 A2 | 12/2007 |
| WO | 2009127260 A1 | 10/2009 |

* cited by examiner

METHOD AND DEVICE FOR THE EARLY DETECTION OF CRACK FORMATIONS IN MEDIA-CARRYING WORKPIECES

CROSS-REFERENCE TO RELATED APPLICATION

This application claims the priority, under 35 U.S.C. §119, of German application DE 10 2013 016 166.5, filed Sep. 30, 2013; the prior application is herewith incorporated by reference in its entirety.

BACKGROUND OF THE INVENTION

Field of the Invention

The invention relates to a device for the early detection of crack formations in work pieces or in components that are subjected to mechanical loading, such as supports, frames, and the like, in particular of media-carrying work pieces that are subjected to an internal pressure in the form of injection-molding tools and the inserts thereof, valves and components thereof, liquid or gas tanks or lines, pressure vessels and lines of power plants as well as hydraulic components or structure-forming parts or drive parts of in particular aircraft, vehicles or ships.

Crack formation of work pieces that are subjected to internal pressure can constitute a problem that has to be taken seriously in many different industrial applications. Therefore, cooling circuits of power plants, which have lines carrying cooling media, are typically monitored continuously with regard to internal pressures. Any defect of the cooling circuit can be identified at an early time by way of a sensed drop in pressure, so that any countermeasures for providing sufficient cooling can be taken. In the area of internal combustion engines, it is customary to provide oil pressure sensors, which continuously monitor the pressure prevailing within components carrying engine oil. A drop in the oil pressure may suggest leakages, in particular defective seals.

It is desirable to detect such defects, and in particular crack formations, at an early time, in particular in cases where escape of a medium carried within the work piece would entail contamination of the vicinity or if there is the risk that, were it to escape, the medium would react highly exothermically and explosively with other components of the vicinity.

In the area of injection-molding technology, injection molding tools such as injection molds and inserts for injection molds that are filled with or flowed around by a liquid melt under high pressure are known. In particular in the case of aluminum die-casting, the injection-molding tools are subjected to high thermal and mechanical loads. If used repeatedly, the inserts often crack. It is particularly problematic that, for cooling, the inserts typically have cooling channels in which water is usually carried as the cooling medium. If the water comes into direct contact with the hot aluminum via cracks, an explosion may occur.

SUMMARY OF THE INVENTION

On the basis of this prior art, an object of the present invention is to provide a device for the early detection of crack formations that makes a reliable and early identification of cracks possible.

It is regarded as the essence of the invention to arrange in the region of at least one surface at risk of cracking at least one testing chamber that is formed by a generative process of manufacturing in a work piece or a portion of a work piece and to which a testing medium under pressure is admitted.

Crack formation in the work piece is either identified by way of a drop in pressure within the testing chamber, which can be sensed by way of a pressure sensor connected to the testing chamber, or sensed by a gas sensor that can react to a testing medium escaping from the testing chamber in the event of crack formation and is arranged in the vicinity of the testing chamber.

Processes that come into consideration particularly as generative manufacturing processes are those in which the work piece or the portion of a work piece is formed layer by layer by building material that can be made to solidify being exposed to radiation. Such manufacturing processes, which are usually referred to as laser sintering or laser melting processes, have the advantage that components can also be manufactured economically in small numbers. Such a generative manufacturing process ensures efficient manufacturing of the work piece or portion of a work piece containing the testing chamber.

It is consequently envisaged either to manufacture the work piece completely by a generative manufacturing process or to manufacture the portion of a work piece that contains the testing chamber in such a way. The latter case concerns what is known as hybrid construction, in which one component of the work piece is manufactured conventionally, for example by molding or milling processes. In a further process step, the portion of a work piece is built up generatively on this component, successive layers of powdered, and in particular metallic, building material being solidified by exposure to radiation. The radiation used for this purpose may contain electron radiation or laser radiation.

In the event of crack formation, a drop in pressure is produced in the testing chamber and can be reliably sensed by the pressure sensor. This correspondingly provides an early detection of crack formations that can be used in many, extremely varied technical areas. Early detection makes it possible in general to be able to respond promptly to the hazardous situation and to initiate adequate countermeasures.

However, the idea essential to the invention is not restricted to detecting crack formation by sensing a drop in pressure in the testing chamber. Rather, it is similarly envisaged to detect crack formation by a gas sensor that is arranged in the vicinity of the testing chamber and can react to the testing medium provided in the testing chamber. Correspondingly, in the case of such embodiments, reactive substances that can be detected in traces by suitable reactions are preferably used as the testing media. An inlet or measuring channel for the arrangement of a pressure sensor is not necessary. Rather, the testing chamber to which the testing medium is admitted can be formed in a closed manner, in order to ensure great mechanical stability of the component. Such a detection of crack formation is therefore suitable in particular for structure-forming components and components that are subjected to mechanical loading.

It goes without saying that the device according to the invention for the early detection of crack formations in media-carrying work pieces can be used advantageously in valves and components thereof, liquid or gas tanks, pressure vessels and lines, in particular of power plants, and in hydraulic components. It is also envisaged to provide structure-forming parts or drive parts of in particular aircraft, vehicles or ships with the crack formation device according to the invention.

In a preferred exemplary embodiment, the testing chamber is arranged under a contour of a work piece that is subjected to compressive loading. For example, the work piece is formed as an insert for a die-casting die, which is exposed to considerable pressures during the die-casting. In the case of this exemplary embodiment, the testing chamber serves the purpose of detecting at an early time whether the liquefied injected material gets into the insert during the die-casting. In another exemplary embodiment, the work piece is formed as a line, which carries for example a pressurized gaseous or liquid medium. The testing chamber is arranged for example in the wall of the line, in order to indicate cracks at an early time. Moreover, a device formed in such a way makes it possible to avoid the gas or liquid medium escaping in the event of crack formation if the pressure prevailing in the testing chamber is greater than the pressures that typically occur in the media-carrying interior space.

The fact that the testing chamber is formed by a generative manufacturing process means that there are many different possibilities for the spatial design of the testing chamber that can be realized economically efficiently. In one exemplary embodiment, the testing chamber is formed by one or more testing lines arranged in the inner region of the work piece in a generative manner. In another exemplary embodiment, the testing chamber is formed by a porous or partly porous inner region of the work piece or by a grid structure formed by individual channel portions. It goes without saying that combinations in which the testing chamber is formed in certain portions by testing lines, a grid structure and/or porous or partly porous inner regions can also be provided. Porous or partly porous regions of the work piece can be created particularly easily by the generative manufacturing processes, in particular laser melting processes, in that the corresponding regions are irradiated with a reduced energy input per unit area, which has the consequence that the powdered metallic building material is at least partly not melted completely. After solidification of the corresponding layer, a porous or partly porous region of the work piece is thus formed.

The density of the individual channel portions is preferably dependent on a potential risk of cracking of the portion of a work piece containing them. Thus, for example, portions of a work piece that are subjected to particularly high pressures or mechanical loads and/or are localized at an exposed place have an increased density of individual channel portions, in order to ensure a reliable early detection of crack formations.

In the case of injection-molding applications, the testing chamber preferably closely follows the contour of a shape-forming inner surface of the injection-molding tool. Correspondingly, the testing chamber extends in the direct vicinity of the inner surface of injection molds and inserts thereof that are subjected to pressure. This achieves the effect that a detection of cracks is made possible before there is any significant damage to the injection-molding tool.

It has proven to be advantageous if the distance between the compressively loaded contour of the work piece, in particular the molded work piece, and the testing chamber extending there under is essentially 1-5 mm.

The work piece may be provided with a cooling channel structure and the testing chamber preferably extends at least in certain regions between the compressively loaded contour of the work piece and the cooling channel structure. Such a work piece may be formed in particular as an injection-molding tool, in particular as an insert for an injection mold. In particular in the case of aluminum die-casting, it is desirable to provide an early detection of cracks, since explosions can occur if the hot aluminum comes into contact with the water carried in the cooling channel structure. The testing chamber lying between the cooling channel structure and the compressively loaded outer contour of the insert makes such an early detection possible. Moreover, further penetration of the melt into the work piece can in this way be counteracted if the testing medium is carried in the testing chamber under pressures that are greater than those pressures with which the die-casting process is carried out.

It has proven to be advantageous in this connection if the testing medium arranged in the testing chamber is not reactive with respect to an injected material that is used in conjunction with the work piece formed as an injection-molding tool. In the case of aluminum die-casting, for example, compressed air may be used as the pressure medium. However, it is also expedient in embodiments that concern liquid or gas tanks, lines, valves or the like to use pressure media that are slow to react, in particular if direct contact with a highly reactive medium must be feared in the event of crack formation.

In a development of the invention it is envisaged to intersperse the testing chamber with pressure-absorbing elements, at least in a region of the contour that is subjected to high loads. These pressure-absorbing elements are formed for example by bridge structures that are directed with their arched regions toward the compressively loaded contour. Such bridge structures can be easily introduced into the work piece during the generative manufacturing process. The pressure-absorbing elements may at least partially compensate for pressure fluctuations that occur locally, so that, in addition to the early detection, the testing chamber is also used for actively counteracting possible crack formation.

The testing chamber is preferably filled with at least partially unsolidified or merely sintered powdered metallic building material. The corresponding regions are consequently not heated beyond a temperature lying above the melting temperature of the metallic building material during the generative manufacturing process.

Preferably connected to the testing chamber is at least one inlet or measuring channel; the measuring channel may for example be configured to receive a pressure-measuring device configured as a probe, in order to sense the pressure conditions existing within the testing chamber.

Compressed air is used with preference as the testing medium in the testing chamber, in particular in applications in which a reaction of the medium with oxygen is not to be feared.

Other features which are considered as characteristic for the invention are set forth in the appended claims.

Although the invention is illustrated and described herein as embodied in a device for the early detection of crack formations in media-carrying work pieces, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
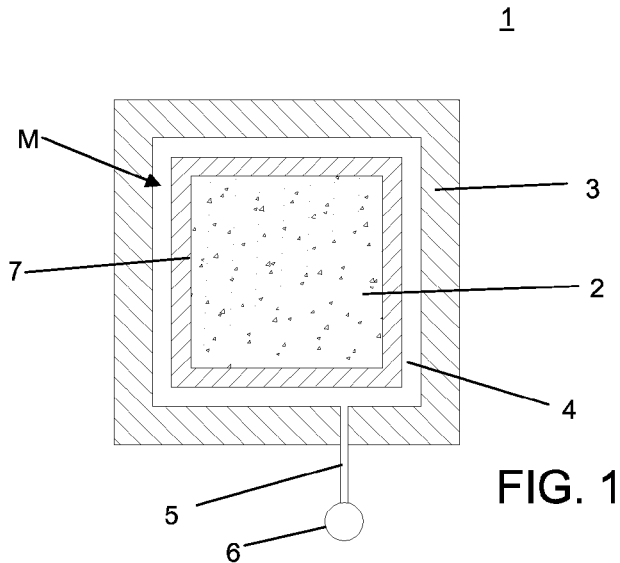
FIG. 1 is a diagrammatic, sectional view of a work piece according to a first exemplary embodiment of the invention, formed as a container.

Parts that correspond to one another are provided with the same designations in all of the figures. Referring now to the figures of the drawings in detail and first, particularly to FIG. 1 thereof, there is shown a work piece 1, which is configured as a container, in a schematic sectional representation. Correspondingly, the work piece 1 has an inner region 2 for receiving a gaseous or liquid medium.

In an exemplary embodiment, the work piece 1 is a pressure vessel, in which a testing medium M is stored in the inner region 2 under conditions of increased pressure in comparison with ambient pressure. Incorporated in a wall 3 of the work piece 1 is a testing chamber 4, which has been formed by a generative manufacturing process. An inlet or measuring channel 5, in which a pressure sensor 6 for measuring the pressure in the testing chamber 4 is provided, is arranged at the testing chamber 4. The pressure prevailing in the testing chamber 4 lies above the pressures prevailing in the inner region 2. Consequently, a crack formation in the portion of the wall 3 that is facing the inner region 2 leads to a rapid drop in pressure, which can be sensed by the pressure sensor 6.

The testing chamber 4 is correspondingly arranged close to the contour at a compressively loaded contour 7 of the work piece 1, so that an early detection of cracks is made possible. The testing chamber 4 contains a multiplicity of testing lines, which form a grid structure that is not represented any more specifically in FIG. 1.

Figure 2:
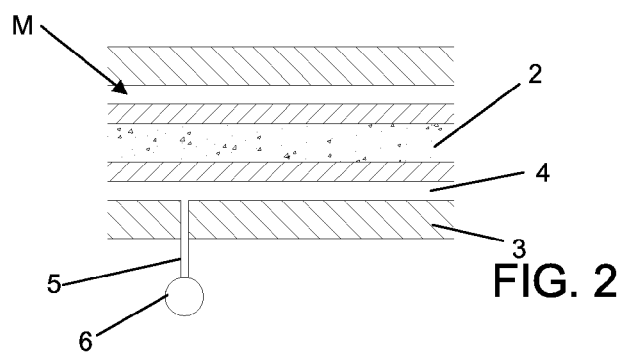
FIG. 2 is a diagrammatic, sectional view of the work piece according to a second exemplary embodiment, configured as a portion of a line.

FIG. 2 shows a further exemplary embodiment, in which the work piece 1 is configured as a portion of a line or pipe. Essential features correspond here to the exemplary embodiment that is already shown in FIG. 1. The work piece 1 of the second exemplary embodiment is formed for carrying a gaseous or liquid medium in the inner region 2. Arranged between a vicinity of the portion of the line and the inner region 2 is the testing chamber 4, in which a pressure that is increased in comparison with the inner region 2 prevails. The pressure in the testing chamber 4 can be monitored continuously by way of the inlet or measuring channel 5 and the pressure sensor 6, so that crack formation can be detected at an early time by detection of a drop in pressure.

According to alternative exemplary embodiments, the testing chamber 4 contains one or more testing lines and/or a portion with a porous or partly porous inner region, which has been manufactured by a generative manufacturing process, in particular a laser sintering and/or laser melting process.

Figure 3:
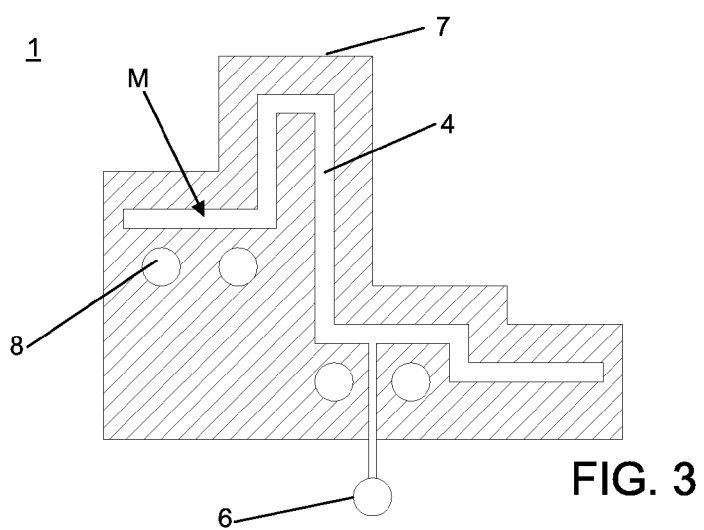
FIG. 3 is a diagrammatic, sectional view of the work piece according to a third exemplary embodiment, formed as an insert of an injection mold.

FIG. 3 shows the work piece 1 according to a further exemplary embodiment that is formed as an insert for an injection mold in a schematic sectional representation. The testing chamber 4 is arranged close to the compressively loaded contour 7, which, when the work piece 1 formed as an insert is used in die-casting, is subjected to an injected material, for example aluminum, in a way that is not represented any more specifically. The distance of the testing chamber 4 from the compressively loaded contour 7 of the work piece 1 in the exemplary embodiment represented by way of example is 4 mm.

It goes without saying that other distances, such as for example distances of a few centimeters down to a few millimeters, are also preferred, depending on the injected materials used and the dimensions of the moldings to be manufactured.

Incorporated in the work piece 1 are cooling channels 8 of a cooling channel structure, which in the use as intended are flushed through with a coolant, in particular water, for the cooling of the work piece 1. The testing chamber 4 is arranged between the cooling channel structure and the compressively loaded contour 7, so that cracks can be detected at an early time, ideally before hot injected material comes into contact with the coolant carried in the cooling channels 8. In a way corresponding to the exemplary embodiments already described, the testing chamber 4 is formed in certain portions by testing lines, which possibly form a grid structure or in certain portions have porous or partly porous inner regions.

Figure 4:
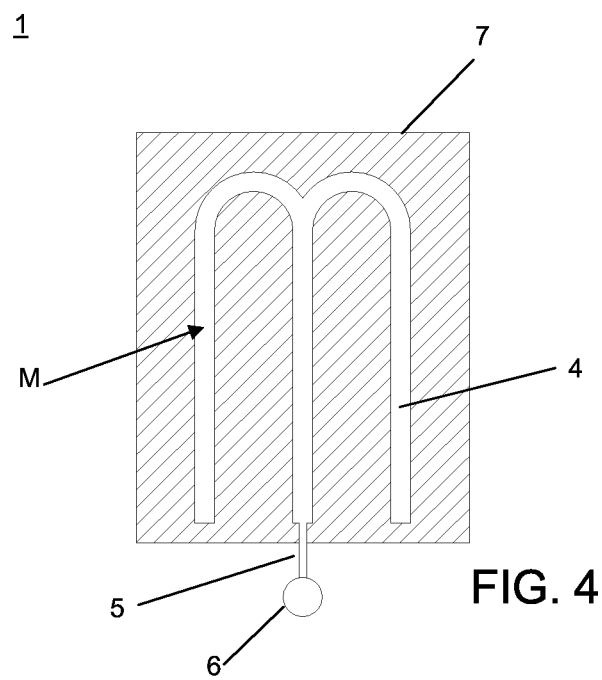
FIG. 4 is a diagrammatic, sectional view of the work piece according to a fourth exemplary embodiment, a testing chamber of which has bridge structures with arched regions that act as pressure-absorbing elements.

FIG. 4 shows a further work piece 1 according to a possible exemplary embodiment of the invention. A schematic cross section through the work piece 1 with the testing chamber 4, which has arch-shaped bridge structures, is shown. The bridge structures are directed with their arched regions in the direction of the compressively loaded contour 7 and act as pressure-absorbing elements, in order to compensate at least partially for the pressures to which the contour 7 is subjected during use of the work piece 1 as intended. According to a specific exemplary embodiment, the work piece 1 shown in FIG. 4 is formed as an insert for use in an aluminum die-casting process.

Figure 5:
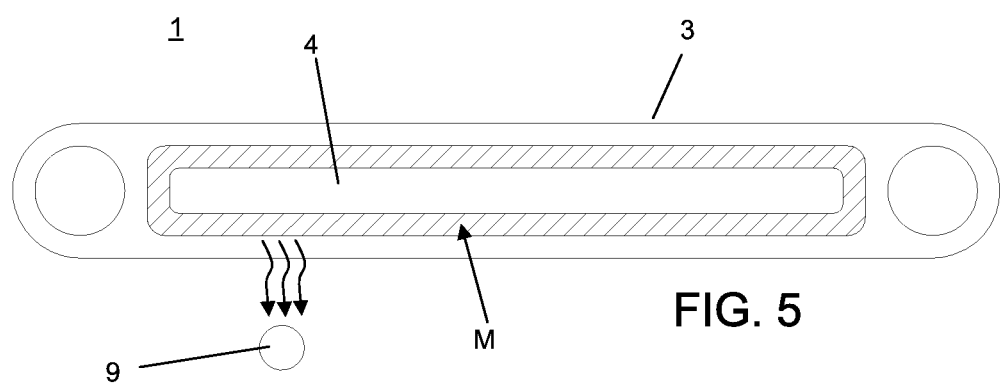
FIG. 5 is a diagrammatic, sectional view of the work piece according to a fifth exemplary embodiment, formed as a longitudinal support, with a partially sintered testing chamber.

FIG. 5 shows a further work piece 1 according to a fifth exemplary embodiment of the invention, configured as a support structure. The work piece 1 shown in a schematic sectional representation in FIG. 6 is configured as a longitudinal support, which has a closed testing chamber 4, in which a reactive and gaseous testing medium M is enclosed under pressure. In the event of crack formation, the testing medium M escaping is chemically detectable by a gas sensor 9. The longitudinal support shown in FIG. 5 has a testing chamber 4, which is partially filled with sintered powdered metallic building material. Such testing chambers can be manufactured by the generative manufacturing process, by the metallic building material not being heated beyond its melting temperature during irradiation.

Figure 6A:
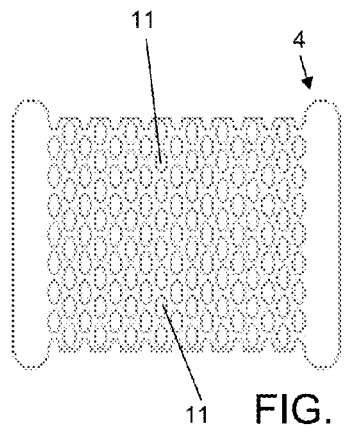
FIGS. 6A-6F are illustrations showing exemplary representations of testing chambers that have a grid structure formed by individual channel portions.
Figure 6B:
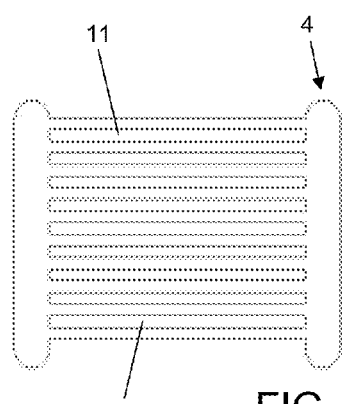
Figure 6C:
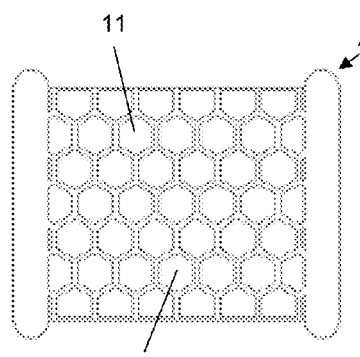
Figure 6D:
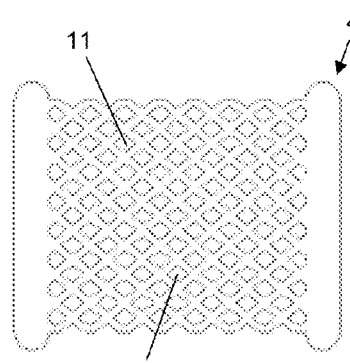
Figure 6E:
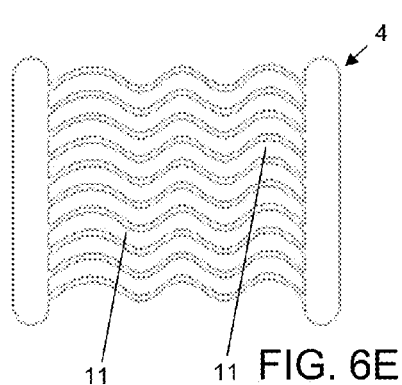
Figure 6F:
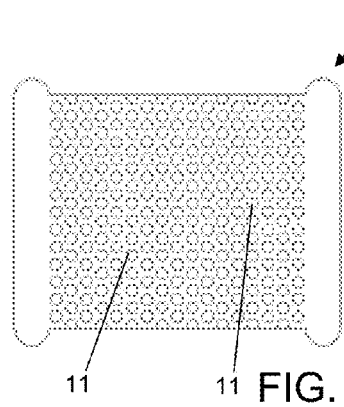

FIGS. 6A-6F schematically show a number of testing chambers 4, which have grid structures formed by individual channel portions. The exemplary embodiments according to FIGS. 6B and 6E show individual channel portions 11 that are not connected to one another transversely. However, all of the testing chambers 4 shown form a sheet-like structure and are suitable for allowing any crack formation to occur over the entire compressively loaded contour 7.

The testing chambers 4 with the grid structures shown in FIGS. 6A, 6C, 6D and 6F have individual channel portions 11 that are also connected to one another in the transverse direction. In this case, regions that have an oval, honeycomb-shaped, rhomboidal or round cross section are formed between the individual channel portions 11.

Depending on the spatial extent of the compressively loaded contour 7 under which the testing chamber 4 is arranged, it is envisaged to vary the density of the individual channel portions 11. In particular, it is envisaged to form the grid structure of the testing chamber 4 in regions of increased loading in such a way that it has in the loaded region a density arrangement of individual channel portions 11 that allows crack formations to be detected at an early time.

In the case of mechanically loaded or structure-forming work pieces 1, it is envisaged to vary the density of the individual channel portions 11 forming the grid structure in dependence on a mechanical loading that is sensed or in particular that is determined by means of simulation.

The following is a summary list of reference numerals and the corresponding structure used in the above description of the invention:
1 Work piece
2 Inner region
3 Wall
4 Testing chamber
5 Inlet channel
6 Pressure sensor
7 Contour
8 Cooling channel
9 Gas sensor
10 Region
11 Individual channel portion
M Testing medium

The invention claimed is:

1. A device for early detection of crack formations in work pieces selected from the group consisting of components, components subjected to mechanical loading, supports, frames, media carrying components subjected to internal pressures, injection-molding tools, inserts of injection-molding tools, valves, components of valves, liquid tanks, gas tanks, gas lines, liquid lines, pressure vessels, lines of power plants, hydraulic components, structure-forming parts, and drive parts for aircraft, vehicles and ships, the device comprising:
  at least one testing chamber disposed in a region of at least one surface at risk of cracking of a work piece, said at least one testing chamber formed in the work piece or a portion of the work piece and having the characteristics of a product formed by a generative process of manufacturing, and to said testing chamber a testing medium under pressure is admitted; and
  a sensor selected from the group consisting of a pressure sensor for determining a drop in pressure resulting from a crack formation in the work piece being connected to said testing chamber and a gas sensor reacting to the testing medium escaping from said testing chamber in an event of the crack formation being disposed in a vicinity of said testing chamber.

2. The device according to claim 1, wherein said testing chamber is disposed under a compressively loaded contour of the work piece.

3. The device according to claim 1, wherein said testing chamber has at least one testing line disposed generatively in an inner region of the work piece.

4. The device according to claim 1, wherein said testing chamber is formed by an inner region of the work piece that is created in the generative manufacturing process by using powdered metallic, and at least partially not completely broken down, building material, and is consequently porous or partially porous.

5. The device according to claim 1, wherein said testing chamber has a grid structure formed by individual channel portions.

6. The device according to claim 5, wherein a density of said individual channel portions is dependent on a potential risk of cracking of a portion of the work piece containing said individual channel portions.

7. The device according to claim 2, wherein said testing chamber closely follows a contour of a shape-forming inner surface of an injection-molding tool.

8. The device according to claim 2, wherein a distance between the compressively loaded contour of the work piece and said testing chamber extending there under is between 1-5 mm.

9. The device according to claim 2, wherein the work piece has a cooling channel structure and said testing chamber extends at least in certain regions between the compressively loaded contour of the work piece and the cooling channel structure.

10. The device according to claim 1, wherein the testing medium disposed in said testing chamber is not reactive with respect to an injected material that is used in conjunction with the work piece formed as an injection-molding tool.

11. The device according to claim 2, wherein said testing chamber is interspersed with pressure-absorbing elements at least in a region of a contour that is subjected to high loads.

12. The device according to claim 11, wherein said testing chamber has as pressure-absorbing elements generatively incorporated bridge structures directed with their arched regions toward the compressively loaded contour.

13. The device according to claim 1, wherein said testing chamber is filled with at least partially unsolidified or merely sintered powdered metallic building material.

14. The device according to claim 1, further comprising at least one inlet or measuring channel connected to said testing chamber.

15. The device according to claim 1, wherein compressed air is used as the testing medium in said testing chamber.

16. A method for manufacturing a device for early detection of crack formations in work pieces selected from the group consisting of components, components subjected to mechanical loading, supports, frames, media carrying components subjected to internal pressures, injection-molding tools, inserts of injection-molding tools, valves, components of valves, liquid tanks, gas tanks, gas lines, liquid lines, pressure vessels, lines of power plants, hydraulic components, structure-forming parts, and drive parts for aircraft, vehicles and ships, which comprises the steps of:
  forming at least one testing chamber in a region of at least one surface at risk of cracking of a work piece, the at least one testing chamber formed by a generative process of manufacturing in the work piece or a portion of the work piece and to the testing chamber a testing medium under pressure is admitted;
  providing a sensor selected from the group consisting of a pressure sensor for determining a drop in pressure resulting from a crack formation in the work piece being connected to the testing chamber and a gas sensor reacting to the testing medium escaping from the testing chamber in an event of the crack formation being disposed in a vicinity of the testing chamber.

* * * * *